United States Patent [19]
Oswald et al.

[11] 3,969,438
[45] July 13, 1976

[54] O,S-DIALKYL-O-CYANOMETHYLPHE-NYLTHIO-PHOSPHATES AND -DITHIOPHOSPHATES

[75] Inventors: Alexis A. Oswald, Mountainside; Paul L. Valint, Jr., Woodbridge, both of N.J.

[73] Assignee: Ciba-Geigy AG, Basel, Switzerland

[22] Filed: Mar. 12, 1975

[21] Appl. No.: 557,557

Related U.S. Application Data
[62] Division of Ser. No. 328,588, Feb. 1, 1973, Pat. No. 3,876,666.

[30] Foreign Application Priority Data
Feb. 1, 1972 Switzerland.......................... 1498/72
Dec. 29, 1972 Switzerland...................... 19075/72

[52] U.S. Cl............................... 260/940; 424/210
[51] Int. Cl.².......................................... C07F 9/18
[58] Field of Search...................................... 260/940

[56] References Cited
UNITED STATES PATENTS
3,825,636  7/1974  Kishino et al................... 260/940 X
3,839,511  10/1974  Kishino et al................... 260/940 X

*Primary Examiner*—Richard L. Raymond
*Attorney, Agent, or Firm*—Frederick H. Rabin

[57] ABSTRACT

Thiolphosphoric acid esters of the formula

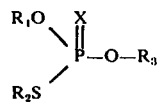

wherein
$R_1$ represents methyl or ethyl,
$R_2$ represents propyl or butyl,
$R_3$ is a radical having the formula:

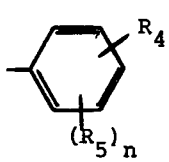

, 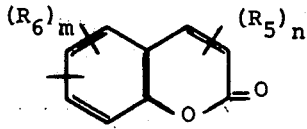

or

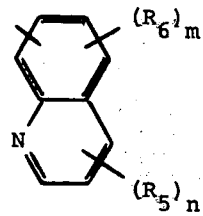

in which
$R_4$ represents allyl, methallyl, -CH$_2$CN, or

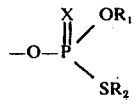

$R_5$ represents hydrogen, halogen, $C_1$-C-alkyl, nitro, cyano, methylmercapto or $C_1$-$C_5$ carboalkoxy,
$R_6$ represents hydrogen, halogen, $C_1$-$C_5$-alkyl or -COCH$_3$,
X represents oxygen or sulphur, and
m and n each denote the number 1 or 2,
process for their production and their use in the control of pests.

3 Claims, No Drawings

O,S-DIALKYL-O-CYANOMETHYLPHENYLTHIO-PHOSPHATES AND -DITHIOPHOSPHATES

CROSS REFERENCE TO RELATED APPLICATION

This is a division of application Ser. No. 328,588 filed Feb. 1, 1973, now U.S. Pat. No. 3,876,666.

DETAILED DISCLOSURE

The present invention relates to thiolphosphoric acid esters, to processes for their production, and to their use in the control of pests.

Substituted phenyl esters of dialkyl thionophosphoric acid, of the formula $(RO)_2P(S)OR'$, represent a very important class of known pesticides. For example, among the phenyl compounds substituted with divalent 2-acryloyloxy groups to form the fused benzopyranyl ring are

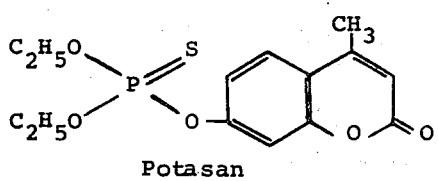

Potasan and

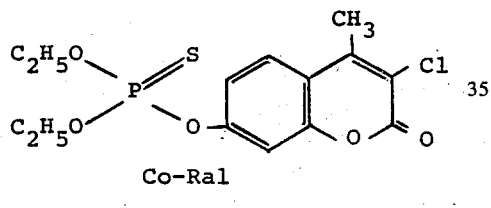

Co-Ral

Potasan is an insecticide described in German Pat. No. 814,297. Co-Ral was first described in German Pat. No. 881,194 and is employed as a pesticide in veterinary medicine. The use of such thionophosphoric acid esters is limited by their generally high toxicity towards warm-blooded animals and their lack of activity against certain pests. It was surprisingly found in the present invention that certain novel thiolphosphoric acid esters, structurally related to these known esters, have a reduced toxicity and broadened pesticidal spectrum.

The unsymmetrically substituted O,S-dialkyl thiolphosphoric acid esters disclosed in the present invention have the formula

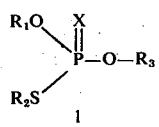

wherein
$R_1$ represents methyl or ethyl,
$R_2$ represents propyl or butyl,
$R_3$ denotes

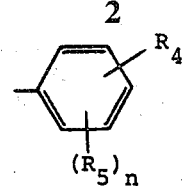

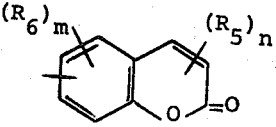

or

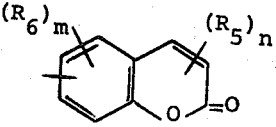

$R_4$ represents allyl, methallyl, $-CH_2CN$, or

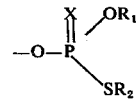

$R_5$ represents hydrogen, halogen, $C_1$-$C_5$-alkyl, nitro, cyano, methylmercapto or carbalkoxy,
$R_6$ represents hydrogen, halogen, $C_1$-$C_5$-alkyl or $-COCH_3$,
X represents oxygen or sulphur, and
m and n each denote the number 1 or 2.

By halogen is meant fluorine, chlorine, bromine and/or iodine, particularly, however, chlorine.

The alkyl groups applicable for formula I can be branched or straight chain. Examples of such groups are: methyl, ethyl, n-propyl, isopropyl, n-, i-, sec.-, tert.-butyl, n-pentyl, and isomers thereof.

From the viewpoint of the unexpected properties of the novel compositions, the choice of the alkyl groups $R_1$ and $R_2$ is most critical. In the related prior art compositions, the alkyl groups (R) are generally identical and equal methyl and ethyl. In the present compounds $R_1$ is methyl or preferably ethyl and $R_2$ is propyl or butyl. Among the $R_2$ groups, the n-propyl and primary i-butyl are preferred. The optimum choice is the O-ethyl S-n-propyl substitution which leads to compounds of decreased toxicity and at the same time increased activity. This finding is in contrast to the structure-biological property correlations observed in the field of the phenyl esters of O,O'-dialkyl thionophosphates wherein the O-ethyl group attributes high toxicity and the O-n-propyl substitution reduces the pesticidal activity. For reference, see Volume 1 of the monograph, "Chemie der Pflanzenshutz — und Schädlingsbekämpfungsmittel" edited by R. Wegler and published by Springer Verlag, New York in 1970, pages 306–324.

An example of the unexpected change of properties is O-ethyl S-n-propyl O'-3-chloro-4-methyl 2-exo-2H-1-benzopyran-7-yl thiolphosphate,

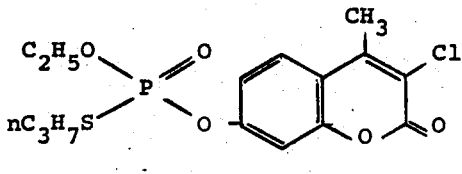

a compound closely related to Co-Ral which shows a high activity against mites and aphids which is completely absent in the case of Co-Ral.

Compounds of formula I preferred because of their unexpected biological properties are compounds wherein
$R_1$ represents ethyl,
$R_2$ represents n-propyl,
$R_3$ represents

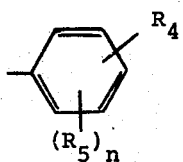

or

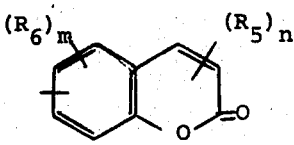

$R_4$ represents allyl, —CH$_2$CN or

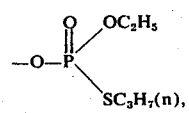

$R_5$ represents hydrogen, chlorine, bromine, cyano, methylmercapto, nitro or methyl,
$R_6$ represents hydrogen, methyl or —COCH$_3$,
X represents oxygen or sulphur, and
m and n each represent the number 1 or 2.

Specifically, preferred types of compounds are those of the formula

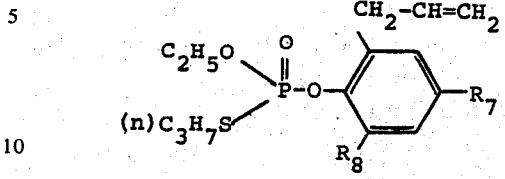

wherein
$R_7$ is chlorine or bromine,
$R_8$ is hydrogen, chlorine, bromine, and

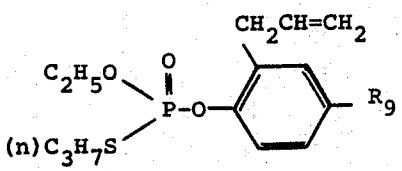

wherein
$R_9$ is nitro, methylthio, cyano, and

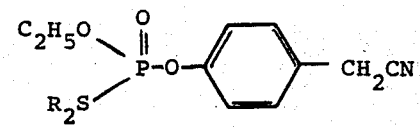

wherein
$R_2$ is n-propyl or i-butyl and

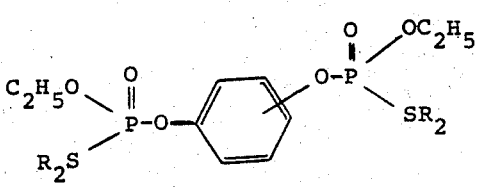

wherein
$R_2$ is n-propyl or i-butyl.

Among the phenyl compounds substituted with the divalent 2-acryloyloxy group to form the fused benzopyranyl ring systems specifically preferred are those of the formula

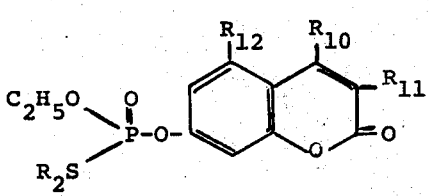

wherein
R$_2$ is n-propyl or i-butyl,
R$_{10}$ is hydrogen or methyl,
R$_{11}$ and R$_{12}$ are hydrogen, chlorine, bromine.

From the phenyl compounds substituted to form a quinoline ring system, the preferred thiolphosphate compounds have no other substituents on the ring.

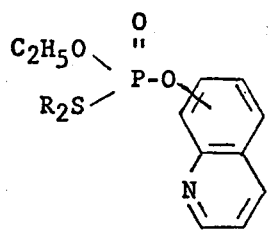

wherein R$_2$ is n-propyl or i-butyl.

Particularly preferred compounds, however, are compounds of formula I wherein
R$_1$ represents ethyl,
R$_2$ represents n-propyl,
R$_3$ represents

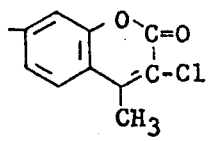

or

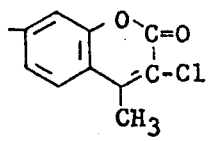

R$_4$ represents allyl, —CH$_2$CN or

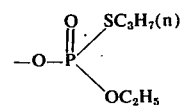

R$_5$ represents hydrogen, chlorine or bromine,
X represents oxygen, and
n represents the number 1 or 2.

The compounds of formula I can be produced by the following methods:

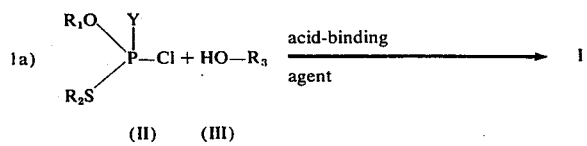

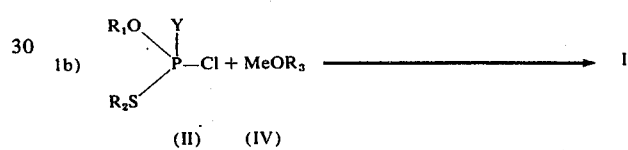

The symbols R$_1$, R$_2$, R$_3$ and Y in formulae II, III and IV have the meanings given in the case of formula I, and Me stands for an alkali metal, particularly for sodium or potassium, or for an ammonium group such as, e.g. the group (R$_4$)$_3$-N$^\oplus$H, wherein R$_4$ represents hydrogen or alkyl.

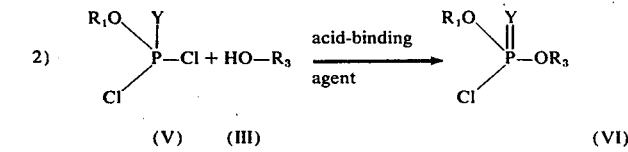

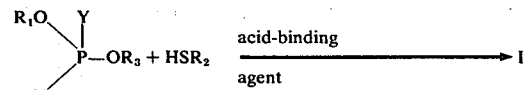

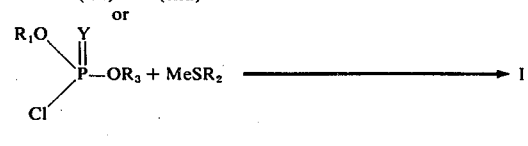

The symbols R$_1$, R$_2$, R$_3$ and Y in formulae II, IIIa, IIIb, V and VI have the meanings given in the case of formula I, and Me stands for an alkali metal, particularly sodium or potassium, or for the group $(R_4)_3\text{-}N^{\oplus}H$, wherein $R_4$ represents hydrogen or $C_1$ to $C_4$ alkyl.

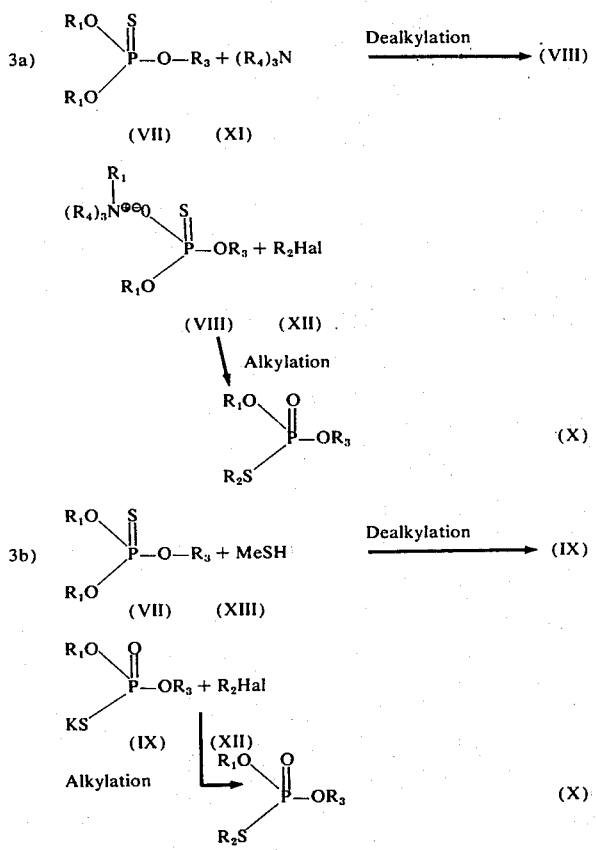

The symbols $R_1$ and $R_3$ in formulae VII to XII have the meanings given in the case of formula I, $R_4$ stands for an alkyl radical, and Hal for a halogen atom such as chlorine, bromine or iodine, and $R_2$ is a primary or secondary propyl or butyl radical, and Me in formula XIII stands for an alkali metal, preferably sodium or potassium.

Suitable acid-binding agents are: tertiary amines, e.g. trialkylamines, pyridine, pyridine bases, dialkylanilines; inorganic bases such as hydrides, hydroxides; carbonates and bicarbonates of alkali metals and alkaline-earth metals.

It is sometimes necessary in performing the reactions to use catalysts, such as, e.g. copper or copper chloride. The processes 1a and 1b, 2 and 3a and 3b are carried out at a reaction temperature of between 0° and 130°C, at normal pressure and in solvents or diluents.

Suitable solvents or diluents are, e.g. ethers and ethereal compounds, such as diethyl ether, dipropyl ether, dioxane, tetrahydrofuran; amides such as N,N-dialkylated carboxylic acid amides; aliphatic, aromatic as well as halogenated hydrocarbons, especially benzene, toluene, xylenes, chloroform, chlorobenzene; nitriles such as acetonitriles; DMSO, ketones such as acetone, methyl ethyl ketone, and water. A further suitable solvent in the case of processes 3a and 3b is ethanol.

The starting materials of formulae II, V and VII can be produced by methods analogous to known methods, e.g. those described in "Organic Reactions II", pp. 1 to 48.

The compounds of formula I have a broad biocidal action, and can be used for the control of diverse plant and animal pests. Surprisingly, they have a better action against, for example, larvae of *Spodoptera littoralis* than analogous compounds from the German Pat. No. 1,164,408 have. Furthermore, the compounds of formula I are suitable also for the control of all development stages, such as, e.g. eggs, larvae, pupae, nymphs and adults of insects of the families: Acrididae, Blattidae, Gryllidae, Gryllotalpidae, Tettigoniidae, Cimicidae, Phyrrhocoridae, Reduviidae, Aphididae, Delphacidae, Diaspidae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae, Pulicidae, as well as acarids of the families: Ixodidae, Argasidae, Tetranychidae, Dermanysidae.

The insecticidal or acaricidal action can be substantially broadened and adapted to suit the given circumstances by the addition of other insecticides and/or acaricides. Suitable additives are, for example, the following active substances:

Organic phosphorus compounds

Bis-O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
O,O-diethyl-O(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE)
O,O-diethyl-S-2-(ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)dithiophosphate (DIMETHOATE)
O,O-dimethyl-O-p-nitrophenylthiophosphate (PARATHION-METHYL)
O,O-diethyl-O- (PARATHION)
O-ethyl-O-p-nitrophenylphenylthiophosphate (EPN)
O,O-dimethyl-O-(4-nitro-m-tolyl)thiophosphate (FENITROTHION)
O,O-dimethyl-O-2,4,5-trichlorophenylthiophosphate (RONNEL)
O-ethyl-O,2,4,5-trichlorophenylethylthiophosphate (TRICHLORONATE)

O,O-dimethyl-O-2,5-dichloro-4-bromophenylthiophosphate (BROMOPHOS)

O,O-dimethyl-O-(2,5-dichloro-4-iodophenyl)-thiophosphate (JODOFENPHOS)

4-tert.butyl-2-chlorophenyl-N-methyl-O-methylamidophosphate (CRUFOMATE)

O,O-dimethyl-O-(3-methyl-4-methylmercaptophenyl)thiophosphate (FENTHION)

Isopropylamino-O-ethyl-O-(4-methylmercapto-3-methylphenyl)phosphate

O,O-diethyl-O-p-(methylsulphinyl)phenyl-thiophosphate (FENSULFOTHION)

O-p-(dimethylsulphamido)phenyl-O,O-dimethylthiophosphate (FAMPHUR)

O,O,O',O'-tetramethyl-O,O'-thiodi-p-phenylenethiophosphate

O-ethyl-S-phenyl-ethyldithiophosphate

O,O-dimethyl-O-($\alpha$-methylbenzyl-3-hydroxycrotonyl)phosphate 2-chloro-1-(2,4-dichlorophenyl)vinyl-diethylphosphate (CHLORFENVINPHOS)

2-chloro-1-(2,4,5-trichlorophenyl)vinyl-dimethylphosphate

O-[2-chloro-1-(2,5-dichlorophenyl)]vinyl-O,O-diethylthiophosphate

Phenylglyoxylonitriloxime-O,O-diethylthiophosphate (PHOXIM)

O,O-diethyl-0-(3-chloro-4-methyl-2-oxo-2-H-1-benzopyran-7-yl)-thiophosphate (COUMAPHOS)

2,3-p-dioxandithiol-S,S-bis(O,O-diethyldithiophosphate) (DIOXATHION)

5-[(6-chloro-2-oxo-3-benzoxazolinyl)methyl]O,O-diethyldithiophosphate (PHOSALONE)

2-(diethoxyphosphinylimino)-1,3-dithiolane

O,O-dimethyl-S-[2-methoxy-1,3,4-thiadiazol-5-(4H)-onyl-(4)-methyl]dithiophosphate O,O-dimethyl-S-phthalimidomethyl-dithiophosphate (IMIDAN)

O,O-diethyl-O-(3,5,6-trichloro-2-pyridyl)thiophosphate

O,O-diethyl-O-2-pyrazinylthiophosphate (THIONAZIN)

O,O-diethyl-O-(2-isopropyl-4-methyl-6-pyrimidyl)-thiophosphate (DIAZINON)

O,O-diethyl-O-(2-quinoxalylthiophosphate

O,O-dimethyl-S-(4-oxo-1,2,3-benzotriazin-3(4H)-ylmethyl)-dithiophosphate (AZINPHOSMETHYL)

O,O-diethyl-S-(4-oxo-1,2,3-benzotriazin-3(4H)-ylmethyl)-dithiophosphate (AZINOPHOSETHYL)

S-[(4,6-diamino-s-triazin-2-yl)methyl]-O,O-dimethyldithiophosphate (MENAZON)

O,O-dimethyl-O-(3-chloro-4-nitrophenyl)thiophosphate (CHLORTHION)

O,O-dimethyl-O(or S)-2-(ethylthioethyl)thiophosphate (DEMETON-S-METHYL)

2-(O,O-dimethyl-phosphoryl-thiomethyl)-5-methoxy-pyrone-4-3,4-dichlorobenzyl-triphenylphosphoniumchloride O,O-diethyl-S-(2,5-dichlorophenylthiomethyl)dithiophosphate (PHENKAPTON)

O,O-diethyl-O-(4-methyl-cumarinyl-7-)-thiophosphate (POTASAN)

5-amino-bis(dimethylamido)phosphinyl-3-phenyl-1,2,4-triazole (TRIAMIPHOS)

N-methyl-5-(O,O-dimethylthiolphosphoryl)-3-thiavaleramide (VAMIDOTHION)

O,O-diethyl-O-[2-dimethylamino-4-methylpyrimidyl-(6)]-thiophosphate (DIOCTHYL)

O,O-dimethyl-S-(methylcarbamoylmethyl)-thiophosphate (OMETHOATE)

O-ethyl-O-(8-quinolinyl)-phenylthiophosphate (OXINOTHIOPHOS)

O-methyl-S-methyl-amidothiophosphate (MONITOR)

O-methyl-O-(2,5-dichloro-4-bromophenyl)-benzothiophosphate (PHOSVEL)

O,O,O,O-tetrapropyldithiophosphate 3-(dimethoxyphosphinyloxy)-N-methyl-N-methoxy-cis-crotonamide O,O-dimethyl-S-(N-ethylcarbamoylmethyl)dithiophosphate (ETHOATE-METHYL)

O,O-diethyl-S-(N-isopropylcarbamoylmethyl)-dithiophosphate (PROTHOATE)

S-N-(1-cyano-1-methylethyl)carbamoylmethyldiethylthiolphosphate (CYANTHOATE)

S-(2-acetamidoethyl)-O,O-dimethyldithiophosphate

Hexamethylphosphoric acid triamide (HEMPA)

O,O-dimethyl-O-(2-chloro-4-nitrophenyl)thiophosphate (DICAPTHON)

O,O-dimethyl-O-p-cyanophenyl thiophosphate (CYANOX)

O-ethyl-O-p-cyanophenylthiophosphate

O,O-diethyl-O-2,4-dichlorophenylthiophosphate (DICHLORFENTHION)

O,2,4-dichlorophenyl-O-methylisopropylamidothiophosphate

O,O-diethyl-O-2,5-dichloro-4-bromophenylthiophosphate (BROMOPHOS-ETHYL)

dimethyl-p-(methylthio)phenylphosphate

O,O-dimethyl-O-p-sulphamidophenylthiophosphate

O-[p-(p-chlorophenyl)azophenyl]O,O-dimethylthiophosphate (AZOTHOATE)

O-ethyl-S-4-chlorophenyl-ethyldithiophosphate

O-isobutyl-S-p-chlorophenyl-ethyldithiophosphate

O,O-dimethyl-S-p-chlorophenylthiophosphate

O,O-dimethyl-S-(p-chlorophenylthiomethyl)dithiophosphate

O,O-diethyl-p-chlorophenylmercaptomethyl-dithiophosphate (CARBOPHENOTHION)

O,O-diethyl-S-p-chlorophenylthiomethyl-thiophosphate

O,O-dimethyl-S-(carbethoxy-phenylmethyl)dithiophosphate (PHENTHOATE)

O,O-diethyl-S-(carbofluorethoxy-phenylmethyl)-dithiophosphate

O,O-dimethyl-S-carboisopropoxy-phenylmethyl)-dithiophosphate

O,O-diethyl-7-hydroxy-3,4-tetramethylene-coumarinyl-thiophosphate (COUMITHOATE)

2-methoxy-4-H-1,3,2-benzodioxaphosphorin-2-sulphide

O,O-diethyl-O-(5-phenyl-3-isooxazolyl)thiophosphate 2-(diethoxyphosphinylimino)-4-methyl-1,3-dithiolane tris-(2-methyl-1-aziridinyl)-phosphine oxide (METEPA)

S-(2-chloro-1-phthalimidoethyl)-O,O-diethyldithiophosphate

N-hydroxynaphthalimido-diethylphosphate dimethyl-3,5,6-trichloro-2-pyridylphosphate O,O-dimethyl-O-(3,5,6-trichloro-2-pyridyl)thiophosphate S-2-(ethylsulphonyl)ethyl dimethylthiolphosphate (DIOXYDEMETON-S-METHYL)

diethyl-S-2-(ethylsulphinyl)ethyl dithiophosphate (OXIDISULFOTON)

bis-O,O-diethylthiophosphoric acid anhydride (SULFOTEP)
dimethyl-1,3-di(carbomethoxy)-1-propen-2-yl-phosphate
dimethyl-(2,2,2-trichloro11butyroyloxyethyl)phosphate (BUTONATE)
O,O-dimethyl-O-(2,2-dichloro-1-methoxy-vinyl)-phosphate
bis-(dimethylamido)fluorphosphate (DIMEFOX)
3,4-dichlorobenzyl-triphenylphosphoniumchloride
dimethyl-N-methoxymethylcarbamoylmethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)phosphate
O-ethyl-S,S-diphenyldithiolphosphate
O-ethyl-S-benzyl-phenyldithiophosphate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl(dithiophosphate
diisopropylaminofluorophosphate (MIPAFOX)
O,O-dimethyl-S-(morpholinylcarbamoylmethyl)dithiophosphate (MORPHOTHION)
bismethylamido-phenylphosphate
O,O-dimethyl-S-(benzenesulphonyl)dithiophosphate
O,O-dimethyl-(S and O)-ethylsulphinylethylthiophosphate
O,O-diethyl-O-4-nitrophenylphosphate
triethoxy-isopropoxy-bis(thiophosphinyl)disulphide
2-methoxy-4H-1,3,2-benzodioxaphosphorin-2-oxide
octamethylpyrophosphoramide (SCHRADAN)
bis-(dimethoxythiophosphinylsulphido)-phenylmethane
N,N,N',N'-tetramethyldiamidofluorophosphate (DIMEFOX)
O-phenyl-O-p-nitrophenyl-methanethiophosphonate (COLEP)
O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethylphenyl)-thiophosphate
4,4'-bis-(O,O-dimethylthiophosphoryloxy)-diphenyl disulphide
O,O-di-(β-chloroethyl)-O-(3-chloro-4-methylcoumarinyl-7-)-phosphate
S-(1-phthalimidoethyl)-O,O-diethyldithiophosphate
O,O-dimethyl-O-(3-chloro-4-diethylsulphamylphenyl)-thiophosphate
O-methyl-O-(2-carbisopropoxyphenyl)-amidothiophosphate
5-O,O-dimethylphosphoryl)-6-chloro-bicyclo(3.2.0)-heptadiene(1,5)
O-methyl-O-(2-i-propoxycarbonyl-1-methylvinyl)-ethylamidothiophosphate.

Nitrophenols and derivatives 4,6-dinitro-6-methylphenol, sodium salt [Dinitrocresol] dinitrobutylphenol-(2,2',2")-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Binapacryl]
2-sec.-butyl-4,6-dinitrophenyl-cyclopropionate
2-sec.-butyl-4,6-dinitrophenylisopropylcarbonate [Dinobuton]

Miscellaneous pyrethin I
pyrethin II
3-allyl-2-methyl-4-oxo-2-cyclopentan-1-yl-chrysanthemumate (Allethrin)
6-chloropiperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxo-1,3-dithiolo-[4,5-b]-quinoxaline (Quinomethionate)
(I)-3-(2-furfuryl)-2-methyl-4-oxocyclopent-2-enyl-(I)-(cis+trans)-chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbamyl-2-trifluoromethylbenzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(5,6)-quinoxaline [Thiochinox]
prop-2-ynyl-(4-t-butylphenoxy)-cyclohexylsulphite [Propargil].

Formamidines 1-dimethyl-2-(2'-methyl-4'-chlorophenyl)-formamidine (CHLORPHENAMIDIN) 1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2"-methyl-4"-chlorophenyl-formamidine
1-n-butyl-2-(2'-methyl-4'-chlorophenyl-imino)-pyrolidine.

Urea

N-2-methyl-4-chlorophenyl-N',N'-dimethyl-thiourea.

Carbamates 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)

5-chloro-6-oxo-2-norborane-carbonitrile-0-(methylcarbamoyl)-oxime 1-(dimethylcarbamoyl)-5-methyl-3-pyrazolyl-N,N-dimethylcarbamate (DIMETILAN)

2,3-dihydro-2,2-dimethyl-7-benzofuranyl-N-methylcarbamate (CARBOFURAN)

2-methyl-2-methylthio-propionaldehyde-0-(methylcarbamoyl)-oxime (ALDICARB)

8-quinaldyl-N-methylcarbamate and its salts methyl-2-isopropyl-4-(methylcarbamoyloxy)carbanilate m-(1-ethylpropyl)phenyl-N-methylcarbamate 3,5-di-tert.butyl-N-methylcarbamate m-(1-methylbutyl)phenyl-N-methylcarbamate 2-isopropylphenyl-N-methylcarbamate 2-sec.butylphenyl-N-methylcarbamate m-tolyl-N-methylcarbamate 2,3-xylyl-N-methylcarbamate 3-isopropylphenyl-N-methylcarbamate 3-tert.butylphenyl-N-methylcarbamate 3-sec.butylphenyl-N-methylcarbamate 3-isopropyl-5-methylphenyl-N-methylcarbamate (PROMECARB)

3,5-diisopropylphenyl-N-methylcarbamate 2-chloro-5-isopropylphenyl-N-methylcarbamate 2-chloro-4,5-dimethylphenyl-N-methylcarbamate 2-(1,3-dioxolan-2-yl)phenyl-N-methylcarbamate (DIOXACARB)

2-(4,5-dimethyl-1,3,-dioxolan-2-yl)phenyl-N-methylcarbamate 2-(1,3-dioxolan-2-yl)phenyl-N,N-dimethylcarbamate 2-(1,3-dithiolan-2-yl)-N,N-dimethylcarbamate 2-(1,3-dithiolan-2-yl)phenyl-N,N-dimethylcarbamate 2-isopropoxyphenyl-N-methylcarbamate (APROCARB)

2-(2-propinyloxy)phenyl-N-methylcarbamate 3-(2-propinyloxy)phenyl-N-methylcarbamate 2-dimethylaminophenyl-N-methylcarbamate 2-diallylaminophenyl-N-methylcarbamate 4-diallylamino-3,5-xylyl-N-methylcarbamate (ALLYXICARB)

4-benzothienyl-N-methylcarbamate 2,3-dihydro-2-methyl-7-benzofuranyl-N-methylcarbamate 3-methyl-1-phenylpyrazol-5-yl-N,N-dimethylcarbamate 1-isopropyl-3-methylpyrazol-5-yl-N,N-dimethylcarbamate (ISOLAN)

2-dimethylamino-5,6-dimethylpyrimidin-4-yl-N,N-dimethyl-carbamate 3-methyl-4-dimethylaminomethyleneiminophenyl-N-methylcarbamate 3,4-dimethylphenyl-N-methylcarbamate 2-cyclopentylphenyl-N-methylcarbamate 3-dimethylamino-methyleneiminophenyl-N-methylcarbamate (FORMETANATE) and its salts 1-methylthio-ethylimino-N-methylcarbamate (METHOMYL)

2-methylcarbamoyloximino-1,3-dithiolane 5-methyl-2-methylcarbamoyloximino-1,3-oxythiolane 2-(1-methoxy-2-propoxy)phenyl-N-methylcarbamate 2-(1-butin-3-yl-oxy)phenyl-N-methylcarbamate 1-dimethylcarbamyl-1-methylthio-0-methylcarbamyl-formoxime 1-(2'-cyanoethylthio)-0-methylcarbamyl-acetaldoxime 1-methylthio-0-carbamyl-acetaldoxime O-(3-sec.butylphenyl)-N-phenylthio-N-methylcarbamate 2,5-dimethyl-1,3-dithiolane-2-(0-methylcarbamyl)-aldoxime O-2-diphenyl-N-methylcarbamate 2-(N-methylcarbamyl-oximino)-3-chloro-bicyclo[2.2.1]heptane 2-(N-methylcarbamyl-oximino)-bicyclo[2.2.1]heptane 3-isopropylphenyl-N-methyl-N-chloroacetal-carbamate 3-isopropylphenyl-N-methylthiomethyl-carbamate O-(2,2-dimethyl-4-chloro-2,3-dihydro-7-benzofuranyl)-N-methylcarbamate O-(2,2,4-trimethyl-2,3-dihydro-7-benzofuranyl)-N-methylcarbamate O-naphthyl-N-methyl-N-acetal-carbamate O-5,6,7,8-tetrahydronaphthyl-N-methyl-carbamate 3-isopropyl-4-methylthio-phenyl-N-methylcarbamate 3,5-dimethyl-4-methoxy-phenyl-N-methylcarbamate 3-methoxymethoxy-phenyl-N-methylcarbamate 3-allyloxyphenyl-N-methylcarbamate 2-propargyloxymethoxy-phenyl-N-methyl-carbamate 2-allyloxyphenyl-N-methyl-carbamate 4-methoxycarbonylamino-3-isopropylphenyl-N-methyl-carbamate 3,5-dimethyl-4-methoxycarbonylamino-phenyl-N-methyl-carbamate 2-γ-methylthiopropylphenyl-N-methyl-carbamate 3-(α-methoxymethyl-2-propenyl)-phenyl-N-met hyl-carbamate 2-chloro-5-tert.-butyl-phenyl-N-methyl-carbamate 4-(methyl-propargylamino-3,5-xylyl-N-methyl-carbamate 4-(methyl-γ-chloroallylamino)-3,5-xylyl-N-methyl-carbamate 4-(methyl-β-chloroallylamino)-3,5-xylyl-N-methyl-carbamate 1-(β-ethoxycarbonylethyl)-3-methyl-5-pyrazolyl-N,N-dimethyl-carbamate 3-methyl-4-(dimethylamino-methylmercapto-methyleneimino)phenyl-N-methylcarbamate 1,3-bis(carbamoylthio)-2-(N,N-dimethylamino)-propanehydrochloride 5,5-dimethylhydroresorcinoldimethylcarbamate 2-[ethyl-propargylamino]-phenyl-N-methylcarbamate 2-[methyl-propargylamino]-phenyl-N-methylcarbamate 2-[dipropargylamino]-phenyl-N-methylcarbamate 4-[dipropargylamino]-3-tolyl-N-methylcarbamate 4-[dipropargylamino]-3,5-xylyl-N-methylcarbamate 2-[allyl-isopropylamino]-phenyl-N-methylcarbamate 3-[allyl-isopropylamino]-phenyl-N-methylcarbamate Chlorinated Hydrocarbons γ-hexachlorocyclohexane [GAMMEXANE; LINDAN; γ HCH]

1,2,4,5,6,7,8,8-octachloro-3α,4,7,7α'tetrahydro-4,7-methylene indane [CHLORDAN]

1,4,5,6,7,8,8,-heptachloro,3α,4,7,7α-tetrahydro-4,7-methylene indane [HEPTACHLOR]

1,2,3,4,10,10-hexachloro-1,4,4α,5,8,8α-hexahydro-endo-1,4-exo-5,8-dimethanonaphthalene [ALDRIN]

1,2,3,4,10,10-hexachloro-6,7-epoxy-1,4,4α,5,6,7,8-,8α-octahydro-exo-1,4-endo-5,8-dimethanonaphthalene [DIELDRIN]

1,2,3,4,10,10-hexachloro-5,7-epoxy-1,4,4α,5,6,7,8-,8α-octahydro-endo-endo-5,8-dimethanonaphthalene [ENDRIN].

In addition to possessing the above mentioned properties, the compounds of formula I are also effective against members of the division Thallophyta. Some of these compounds thus have a bactericidal action. They are particularly effective, however, against fungi, especially against phytophathogenic fungi belonging to the following classes: Oomycetes, Zygomycetes, Ascomycetes, Basidiomycetes and Denteromycetes. The compounds of formula I have moreover a fungitoxic action in the case of fungi which attack plants from the soil. Furthermore, the new active substances are suitable for the treatment of seeds, fruits, tubers, and so forth, to obtain protection against fungus infections. The compounds of formula I are suitable also for the control of phytophathogenic nematodes.

The compounds of formula I can be used on their own or together with suitable carriers and/or additives. Suitable carriers and additives may be solid or liquid, and correspond to the substances common in formulation practice, such as, e.g. natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays, or solutions, the formulation of these preparations being effected in a manner commonly known in practice. Also to be mentioned are cattle dips and spray races, in which aqueous preparations are used.

The agents according to the invention are produced in a manner known per se by the intimate mixing and/or grinding of active substances of formula I with the suitable carriers, optionally with the addition of dispersing agents or solvents which are inert to the active substances. The active substances can be obtained and used in the following preparation forms:

solid preparations: dusts, scattering agents, granulates, coated granulates, impregnated granulates and homogeneous granulates;

liquid preparations:

a. water dispersible active substance concentrates: wettable powders, pastes, emulsions;

b. solutions.

The solid preparations (dusts, scattering agents) are produced by the mixing of the active substances with solid carriers. Suitable carriers are, e.g. kaolin, talcum, bole, loess, chalk, limestone, ground limestone, attapulgite, dolomite, diatomaceous earth, precipitated silicic acid, alkaline-earth silicates, sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Granulates can be very easily prepared by a process in which an active substance of formula I is dissolved in an organic solvent, the thus obtained solution applied to a granulated mineral, e.g. attapulgite, $SiO_2$, granicalcium, bentonite, etc., and the organic solvent then evaporated off.

It is possible also to produce polymer granulates; in this case the active substances of formula I are mixed with polymerisable compounds (urea/formaldehyde; dicyandiamide/formaldehyde; melamine/formaldehyde, or others); polymerisation is then carefully carried out in a manner which leaves the active substances unaffected, and granulation performed actually during the gel forming process. It is more favourable, however, to impregnate finished porous polymer granules (urea/formaldehyde, polyacrylonitrile, polyester and others), having a specific surface area and a favourable predeterminable adsorption/desorption ratio, with the active substances, e.g. in the form of their solutions (in a low-boiling solvent), and to then remove the solvent. Polymer granulates of this kind can be also sprayed in the form of microgranulates, having bulk weights of preferably 300 g/liter to 600 g/liter, with the aid of spray apparatus. Spraying can be carried out over extensive areas of useful plant crops by the use of aeoplanes.

Granulates can also be obtained by the compacting of the carrier material with the active substances and additives, and a subsequent reducing operation.

Moreover, it is possible to add to these mixtures additives stabilising the active substance and/or nonionic, anion-active and cation-active substances which improve, e.g. the adhesiveness of the active substances on plants and parts of plants (adhesives and agglutinants), and/or ensure a better wettability (wetting agents) as well as dispersibility (dispersing agents).

The following substances are, for example, suitable: olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acid, the alkali metal and alkaline-earth metals salts thereof, polyethylene glycol ethers (carbowaxes), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea and formaldehyde, as well as latex products.

Water-dispersible concentrates of active substances, i.e. wettable powders, pastes and emulsion concentrates, are agents which can be diluted with water to obtain any desired concentration. They consist of active substance, carrier, optionally additives which stabilise the active substance, surface-active substances, and anti-foam agents and, optionally, solvents.

The wettable powders and pastes are obtained by the mixing and grinding of the active substances with dispersing agents and pulverulent carriers, in suitable devices, until homogeneity is obtained. Suitable carriers are, e.g. those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of napthalene or of naphthalenesulphonic acids with phenol and formaldehyde, as well as alkali, ammonium and alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, diteriary ethylene glycols, dialkyl dilauryl ammonium chloride, and fatty acid alkalimetal and alkaline-earth metal salts.

Suitable anti-foam agents are, e.g. silicones.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g. alcohols, benzene, xylene, toluene, dimethylsulphoxide, and mineral oil fractions boiling in the range of 120° to 350°C. The solvents must be practically odourless, nonphytotoxic, and inert to the active substances.

Furthermore, the agents according to the invention can be used in the form of solutions. For this purpose, the active substance, or several active substances, of the general formula I is dissolved in suitable organic solvents, solvent mixtures, or water. As organic solvents it is possible to use aliphatic and aromatic hydrocarbons, their chlorinated derivatives, alkylnaphthalenes, mineral oils on their own or in admixture with each other.

The content of active substance in the above described agents is between 0.1 and 95%; it is to be mentioned in this connection that in the case of application of the agents from an aeroplane, or by means of some other suitable application devices, concentrations of up to 99.5% can be used, or even the pure active substance.

The active substances of formula I can be prepared, e.g. as follows:

Dusts

The following substances are used for the preparation of (a) a 5% dust, and (b) a 2% dust:

a.
5 parts of active substance
95 parts of talcum.

b.
2 parts of active substance
1 part of highly dispersed silicic acid
97 parts of talcum.

The active substances are mixed and ground with the carriers.

Granulate

The following substances are used to produce a 5% granulate:

5 parts of active substance,
0.25 parts of epichlorhydrin,
0.25 parts of cetyl polyglycol ether,
3.50 parts of polyethylene glycol,
91 parts of kaolin (particle size 0.3 – 0.8 mm).

The active substance is mixed with epichlorhydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder

The following constituents are used for the preparation of (a) a 40%, (b) and (c) a 25%, and (d) a 10% wettable powder:

a.
40 parts of active substance,
5 parts of sodium lignin sulphonate,
1 part of sodium dibutyl-naphthalene sulphonate,
54 parts of silicic acid.

b.
25 parts of active substance,
4.5 parts of calcium lignin sulphonate
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin.

c.
25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin.

d.
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce (a) a 10% and (b) a 25% emulsifiable concentrate:

a.
10 parts of active substance,
3.4 parts of epoxidised vegetable oil,
13.4 parts of a combination emulsifier consisting of fatty alcohol polyglycol ether and alkylarylsulphonate calcium salt,
40 parts of dimethylformamide,
43.2 parts of xylene.

b.
25 parts of active substance,
2.5 parts of epoxidised vegetable oil,
10 parts of an alkylarylsulphonate/fatty alcoholpolyglycol ether mixture
5 parts of dimethylformamide,
57.5 parts of xylene.

From these concentrates it is possible to produce, by dilution with water, emulsions of any desired concentration.

Spray

The following constituents are used to prepare a 5% spray:

5 parts of active substance,
1 part of epichlorhydrin, 94 parts of ligroin (boiling limits 160°–290°C).

EXAMPLE 1

O-Ethyl-S-n-propyl-0-(2-allyl-4-chlorophenyl)-thiolphosphate

An amount of 10.12 g of triethylamine is added to a solution of 16.86 g of 2-allyl-4-chlorophenol (B.P. 133°C/16 Torr) in 100 ml of benzene. An addition is then made dropwise at 10° – 15°C, with continuous stirring, of 20.3 g of O-ethyl-S-n-propylthiophosphoric acid chloride; stirring is subsequently continued for 12 hours at room temperature. The mixture is washed with water, with a 3% $Na_2CO_3$ solution, and again with water, and dried over anhydrous sodium sulphate. The benzene is distilled off and the residue purified by means of molecular distillation. There is thus obtained the compound of the formula

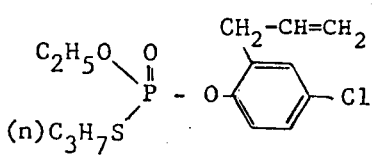

having a refraction of $n_D^{20} = 1.5306$ and a B.P. of 124°C/0.1 Torr.

The following compounds too are obtained in an analogous manner:

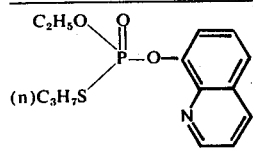   $n_D^{20}$: 1.5765

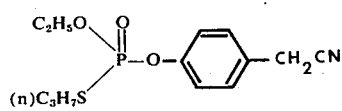   $n_D^{20}$: 1.5262

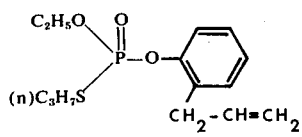   $n_D^{20}$: 1.5213

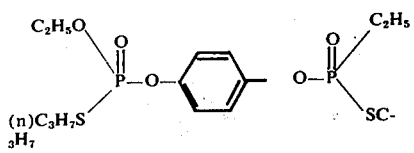   $n_D^{20}$: 1.5205

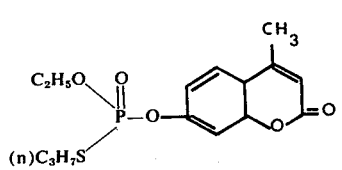   $n_D^{20}$: 1.5694

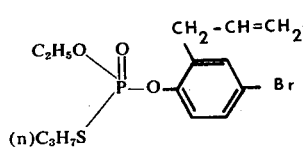   $n_D^{20}$: 1.5444

-continued

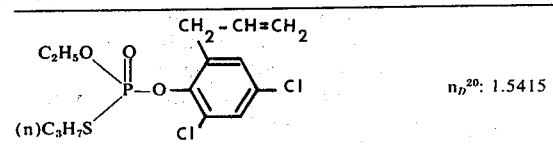   $n_D^{20}$: 1.5415

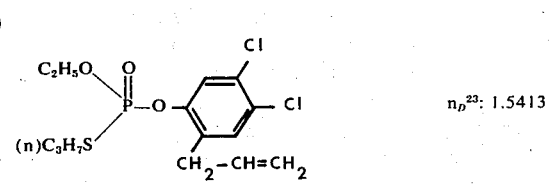   $n_D^{23}$: 1.5413

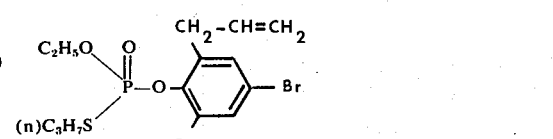

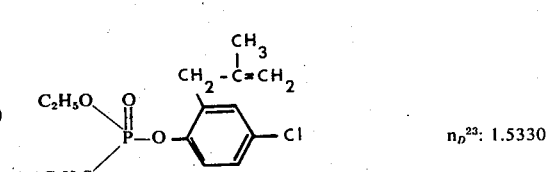   $n_D^{23}$: 1.5330

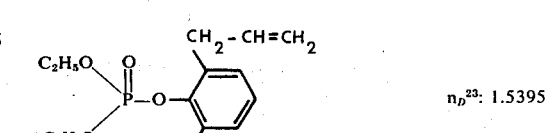   $n_D^{23}$: 1.5395

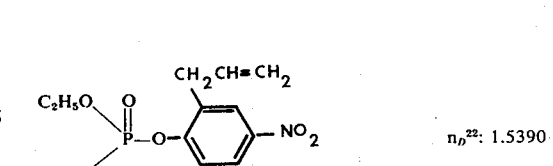   $n_D^{22}$: 1.5390

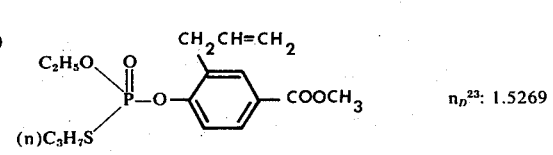   $n_D^{23}$: 1.5269

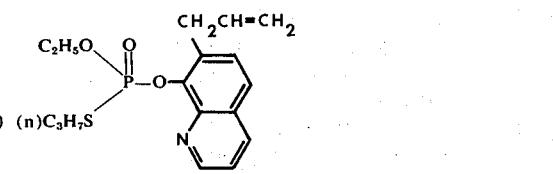

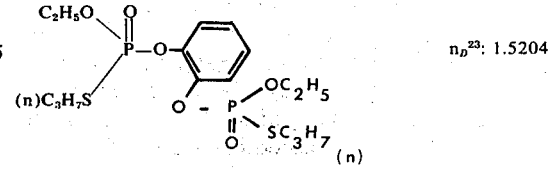   $n_D^{23}$: 1.5204

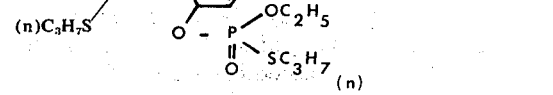

3,969,438
21
-continued
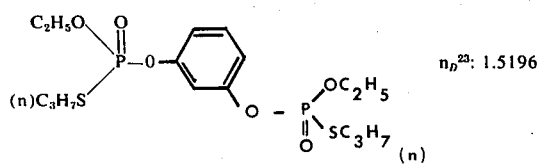 $n_D^{23}$: 1.5196
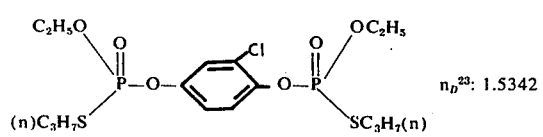 $n_D^{23}$: 1.5342
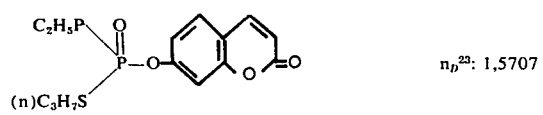 $n_D^{23}$: 1.5707
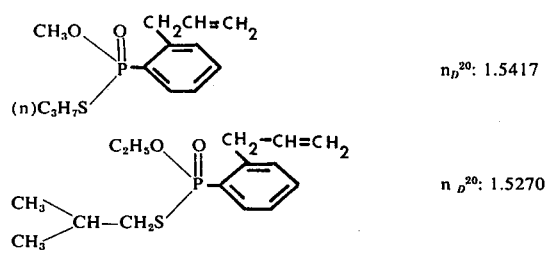 $n_D^{20}$: 1.5417
$n_D^{20}$: 1.5270
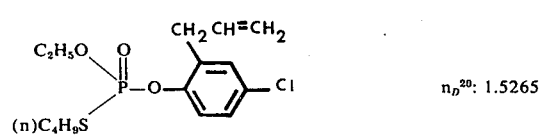 $n_D^{20}$: 1.5265
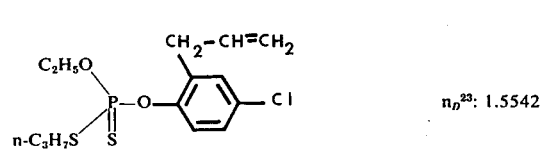 $n_D^{23}$: 1.5542
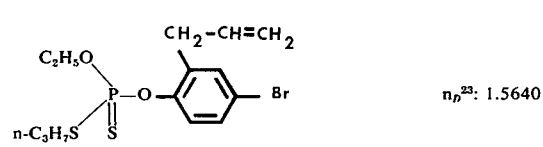 $n_D^{23}$: 1.5640
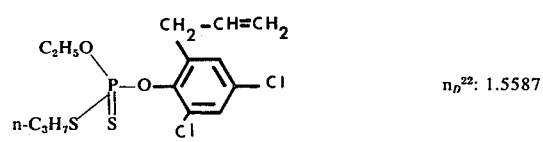 $n_D^{22}$: 1.5587
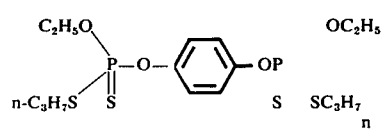
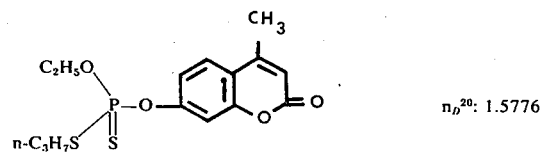 $n_D^{20}$: 1.5776
22
-continued
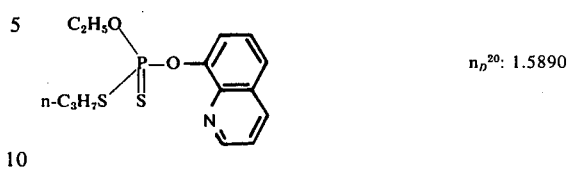 $n_D^{20}$: 1.5890
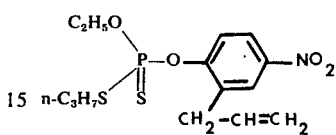
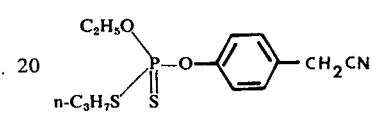
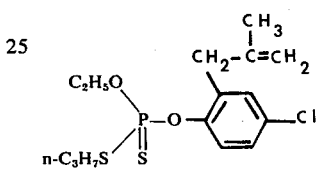
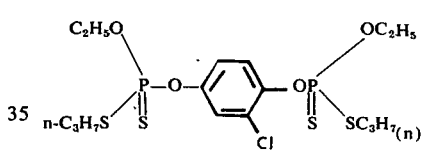
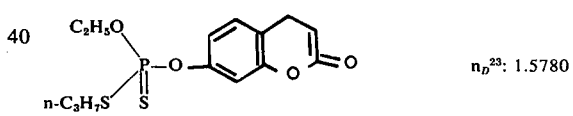 $n_D^{23}$: 1.5780
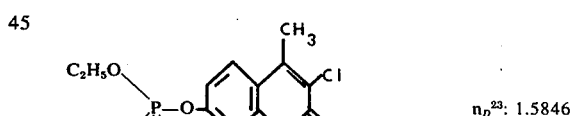 $n_D^{23}$: 1.5846
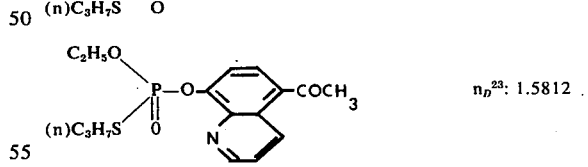 $n_D^{23}$: 1.5812
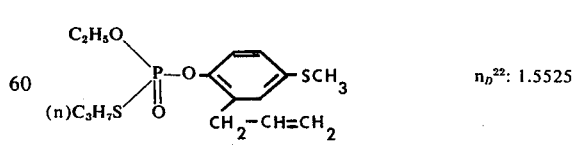 $n_D^{22}$: 1.5525
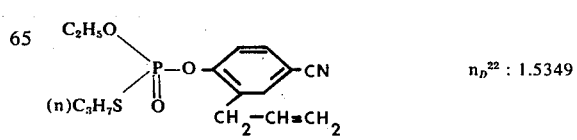 $n_D^{22}$: 1.5349

3,969,438

23
-continued

| Structure | Property |
|---|---|
| (n)C₃H₇S, O, P-O-[phenyl with CH=CH-O-C=O ring, Br], C₂H₅O | M.P.: 56°C |
| (n)C₃H₇S, O, P-O-[phenyl with Cl, CH₂-C(CH₃)=CH₂], C₂H₅O | $n_D^{23}$: 1.5330 |
| (n)C₃H₇S, O, P-O-[phenyl with CH₂-CH=CH₂, CH₃], C₂H₅O | $n_D^{23}$: 1.5215 |
| (n)C₃H₇S, O, P-O-[phenyl with Cl, CH₂-CH=CH₂], C₂H₅O | $n_D^{23}$: 1.5335 |
| (n)C₃H₇S, O, P-O-[phenyl with Cl, Cl, CH₂-CH=CH₂], C₂H₅O | $n_D^{23}$: 1.5412 |
| (n)C₃H₇S, O, P-O-[phenyl with Cl, Cl, CH₂-CH=CH₂], C₂H₅O | $n_D^{23}$: 1.5418 |
| (n)C₃H₇S, O, P-O-[phenyl with CH₃, CH ring, O-C=O], C₂H₅O | $n_D^{23}$: 1.5673 |

EXAMPLE 2

A. Insecticidal stomach poison action

Cotton and potato plants were sprayed with a 0.05% aqueous active-substance emulsion (obtained from a 10% emulsifiable concentrate).

After the drying of the obtained coating, Spodoptera litoralis or Heliothis virescens larvae L₃ were placed onto the cotton plants, and Colorada bettle larvae (Leptinotarsa decemlineata) onto the potato plants. The test was carried out at 24°C with 60% relative humidity.

The compounds according to Example 1 exhibited in the above test a good insecticidal stomach poison action against Spodoptera litoralis, Heliothis and Leptinotarsa decemlineata larvae.

B. Systemic insecticidal action

In order to determine the systemic action, rooted bean plants (Vicia faba) were placed into a 0.01% aqueous active-substance solution (obtained from a 10% emulsifiable concentrate). After a period of 24 hours, bean aphids (Aphis fabae) were placed onto the parts of the plants above the soil. The insects were protected by a special device from the effects of contact and of gas. The test was carried out at 24°C with 70% relative humidity.

In the above tests, the compounds according to Example 1 exhibited a systemic action against Aphis fabae.

EXAMPLE 3

Action against Chilo suppressalis

Rice plants of the Caloro were planted, 6 plants per pot, in plastic pots having a top diameter of 17 cm, and grown to a height of ca. 60 cm. Infestation with Chilo suppressalis larvae (L₁; 3–4 mm long) was carried out 2 days after application of the active substance in granular form (amount applied = 8 kg of active substance per hectare) to the paddy water. The evaluation of the insecticidal action was made 10 days after application of the granules.

The compounds according to Example 1 were effective against Chilo suppressalis in the above test.

EXAMPLE 4

Action against ticks

A. Rhipicephalus bursa

In each case, 5 adult ticks or 50 tick larvae were placed into a small glass test tube, and the test tubes then immersed for 1 to 2 minutes in 2 ml of an aqueous emulsion from a dilution series of 100, 10, 1 and 0.1 ppm of test substance. The tubes were then sealed with a standardised cotton plug, and inverted so that the active substance emulsion could be absorbed by the cotton wool.

An evaluation in the case of the adults was made after 2 weeks, and in the case of the larvae after 2 days. There were two repeats for each test.

B. Boophilus microplus (larvae)

With a dilution series analogous to that in Test A, tests were carried out with 20 sensitive larvae and OP-resistant larvae, respectively (resistance is with respect to diazinon compatibility).

The compounds according to Example 1 were effective in these tests against adults and larvae of Rhipicephalus bursa and against sensitive and OP-resistant larvae, respectively, of Boophilus microplus.

EXAMPLE 5

Acaricidal action

Phaseolus vulgaris (plants) were infested, 12 hours before the test for acaricidal action, with an infested piece of leaf from a mass culture of Tetranychus urticae. The transferred mobile stages were sprayed with the emulsified test preparations from a chromatography-sprayer in a manner ensuring no running off of the spray liquor. An assessment was made after 2 to 7 days, by examination under a binocular, of the living and of the dead larvae, adults and eggs, and the results expressed in percentages. The treated plants were kept during the "holding time" in greenhouse compartments at 25°C.

The compounds according to Example 1 were effective in the above test against adults, larvae and eggs of *Tetranychus urticae*.

EXAMPLE 6

Action against soil nematodes

In order to test the action against soil nematodes the active substances were added, in the concentration stated in each case, to soil infested with root-gall-nematodes (Meloidogyne arenaria), and the whole intimately mixed. In the one test series, tomato seedlings were planted immediately afterwards in the thus prepared soil, and in the other test series tomatoes were planted after a waiting time of 8 days.

For an assessment of the nematicidal action, the galls present on the roots were counted 28 days after planting and sowing, respectively.

The active substances according to Example 1 exhibited in this test a good action against *Meloidogyne arenaria*.

EXAMPLE 7

Action against *Botrytis cinerea* on Vicia faba

In Petri dishes lined with moist filter paper were placed, in each case, three fully developed, identically large leaves of *Vicia faba* which had been sprayed until dripping wet with a liquor prepared from the active substance in the form of a 10% wettable powder (content of active substance in the liquor = 0.1%), spraying being effected by means of a spraying apparatus. When the leaves were again dry, they were infested with a freshly prepared, standardized spore suspension of the fungus (concentration: 100,000 spores/ml), and kept for 48 hours in a moist atmosphere at 20°C. The leaves exhibited after this period of time firstly point-like spots, which then rapidly spread. The number and size of the areas of infection served as a criterion in the assessment of the effectiveness of the test substance.

The compounds according to Example 1 were effective in the above test against Botrytis cinerea.

EXAMPLE 8

O-Ethyl S-n-Propyl 0-3-Chloro-4-Methly 2-Exo-2H-1-Benzopyran-7-yl Thiophosphate O,O'-Diethyl-0-3-chloro-4-methly-2-exo-2H-1-benzopyran 7-yl thiophosphate (38.25 g., 0.1 mole) and 11.2 g. (0.1 mole) of 1,4-di-azabicylo [2.2.2] octane (triethylene diamine) were dissolved in 500 ml. of acetonitrile. The solution was left to stir at ambient temperature for 24 hrs. To the solution, 24.6 g. (0.2 mole) of 1-bromopropane were added and mixture was heated to 70°C for 24 hrs. A solid precipitated which was removed by filtration. The filtrate was concentrated under reduced pressure and the residue was dissolved in 500 ml. of ether. The ether solution was washed with water and 5% aqueous sodium bicarbonate and dried over anhydrous magnesium sulfate. The solvent was removed under vacuum (0.1 mm) to give 10.6 g. of residue. The structure of the product was confirmed by nuclear magnetic resonance (nmr) spectroscopy as being:

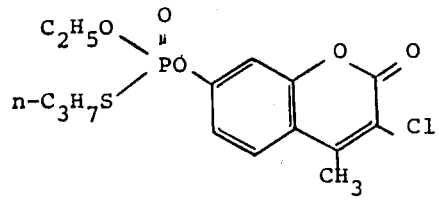

Analyses Calcd. for $C_{15}H_{18}ClO_5PS$: C, 45.57; H, 4.55; P, 7.84; Cl, 8.95; Found: C, 47.38; H, 4.85; P, 8.20; Cl, 9.06.

EXAMPLE 9

Comparative Biological Testing of O-Ethly S-n-Propyl Thiolphosphate and Related O,O'-Diethly Thionophosphate The thiolphosphate described in Example 8 and the related thionophosphate Co-Ral described in the specification were tested as aqueous emulsions containing 100 ppm active compound each using the following methods:

Mites, Contact: Potted bean plants infested with the two-spotted spider mite were placed on a turntable and sprayed with a formulation of the test chemical. The plants were held for 5 days and the degree of mite control was rated after 2 days.

Mites, Systemic: Bean plants infested with the two-spotted mites were treated by applying 20 ml. of the formulated test chemical to the soil.

Aphid, Contact: Potted nasturtium plants infested with the bean aphids were placed on a turntable and sprayed with a formulation of the test chemical. The plants were held for 2 days and the degree of aphid control was rated.

Results: It was found that the thiolphosphate produced a complete control in all the above tests while no control whatsoever was observed for the thionophosphate.

We claim:

1. A compound of the formula

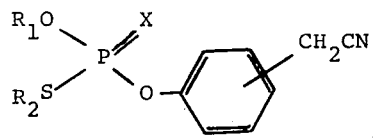

wherein $R_1$ is methyl or ethly, $R_2$ is propyl or butyl, and X is oxygen or sulphur.

2. A compound according to claim 1 in which $R_1$ is ethyl, $R_2$ is n-propyl or isobutyl, X is oxygen and the group —$CH_2CN$ is in the 4-position.

3. The compound of claim 2 which is O-ethyl-S-n-propyl-O-(4-cyanomethylpheny)-thiophosphate.

* * * * *